United States Patent
McCord

(10) Patent No.: US 7,710,556 B1
(45) Date of Patent: May 4, 2010

(54) INSPECTION SYSTEM

(75) Inventor: Mark A. McCord, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 223 days.

(21) Appl. No.: 11/752,958

(22) Filed: May 24, 2007

(51) Int. Cl.
*G01N 21/00* (2006.01)

(52) U.S. Cl. .............. 356/237.1; 356/237.2; 356/237.6; 414/792.9; 414/796.7; 414/797.5; 414/246; 414/281

(58) Field of Classification Search ... 356/237.1–237.6, 356/356; 250/231.16, 237; 414/792.9, 796.7, 414/797.5, 246, 281
See application file for complete search history.

(56) References Cited

U.S. PATENT DOCUMENTS

| | | | | |
|---|---|---|---|---|
| 5,005,089 A | * | 4/1991 | Thanos et al. | 360/77.08 |
| 5,084,791 A | * | 1/1992 | Thanos et al. | 360/77.04 |
| 5,146,085 A | * | 9/1992 | Ishizuka et al. | 250/231.16 |
| 5,477,402 A | * | 12/1995 | Elliott et al. | 360/77.08 |
| 6,137,646 A | * | 10/2000 | Okamura et al. | 360/51 |
| 2003/0090681 A1 | * | 5/2003 | Jones et al. | 356/614 |
| 2006/0098327 A1 | * | 5/2006 | Ehrlich et al. | 360/75 |
| 2006/0156171 A1 | * | 7/2006 | Kuznetsov et al. | 714/755 |

* cited by examiner

*Primary Examiner*—Tarifur R. Chowdhury
*Assistant Examiner*—Isiaka O Akanbi
(74) *Attorney, Agent, or Firm*—Luedeka, Neely & Graham, P.C.

(57) ABSTRACT

A substrate inspection system of a type that receives substrates disposed within a cassette and inspects a planar surface of the substrates with a read head, where the substrates are inspected while they are disposed within the cassette, and the read head is of a size to fit between adjacent substrates within the cassette. In this manner, the substrates do not need to be removed from the cassette, and no robotic arm is required to do so.

8 Claims, 3 Drawing Sheets

INSPECTION SYSTEM

FIELD

This invention relates to the field of integrated circuit fabrication. More particularly, this invention relates to inspecting the substrates on which integrated circuits are fabricated.

BACKGROUND

Integrated circuits are often formed on substrates, such as substrates of semiconducting material. Such substrates can hold as few as one or many as thousands of the integrated circuits. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

Integrated circuits are typically formed in a series of process steps, where materials are first added to the substrate in layers, then patterned, and finally etched or otherwise altered before another layer is added. Typically it is extremely difficult to go back and fix a layer that has been improperly formed, after another layer has been formed on top of the malformed layer. For this and other reasons, the substrates are usually given frequent and thorough inspections, such as optical inspections.

A substrate is typically inspected by removing the substrate from the cassette in which it and other substrates are held, and moving the substrate into an inspection system. This substrate handling is usually performed by a robot arm that has been fitted with a head that can engage the substrate. The inspection system typically includes a motorized stage that moves the substrate around underneath the inspection optics. The inspection optics remain in one place, because they tend to include large glass lenses that—because of their weight, size, and delicate nature—cannot be moved as easily as the substrate. Once the inspection is complete, the robot arm removes the substrate from the stage and places it back into the cassette, from which another substrate is removed, and the inspection process is repeated.

Unfortunately, the robot arms required to move the substrates tend to be rather expensive. Further, moving the substrates around in this manner tends to require an appreciable amount of time.

What is needed, therefore, is a system that overcomes problems such as those described above, at least in part.

SUMMARY

The above and other needs are met by a substrate inspection system of a type that receives substrates disposed within a cassette and inspects a planar surface of the substrates with a read head, where the substrates are inspected while they are disposed within the cassette, and the read head is of a size to fit between adjacent substrates within the cassette. In this manner, the substrates do not need to be removed from the cassette, and no robotic arm is required to do so.

In various embodiments according to this aspect of the invention, relative movement between the substrate and the read head produces scan lines that are assembled into an inspection image of the substrate. In some embodiments, movement of only the substrate relative to the read head produces the scan lines that are assembled into an inspection image of the substrate. In other embodiments, movement of only the read head relative to the substrate produces the scan lines that are assembled into an inspection image of the substrate. In yet other embodiments, movement of both the substrate and the read head produces the scan lines that are assembled into an inspection image of the substrate. An air bearing is disposed on the read head in some embodiments, where the air bearing rides along the surface of the substrate and sets a working distance between the substrate and the read head. Some embodiments have multiple read heads, where the substrate inspection system is operable to simultaneously inspect more than one substrate while the substrates are disposed within the cassette.

According to another aspect of the invention there is described a substrate inspection system of a type that receives substrates disposed within a cassette and inspects a planar surface of the substrates at a working distance with a read head, where the working distance is set with an air bearing disposed on the read head, and the air bearing rides along the surface of the substrate.

According to yet another aspect of the invention there is described a substrate inspection system of a type that receives substrates disposed within a cassette and inspects a planar surface of the substrates with a read head, where the substrate is inspected by scanning the read head across the surface of the substrate while the substrate remains stationary.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

According to various embodiments of the present invention, the substrate to be inspected remains in the cassette during the inspection process. In prior art inspection systems, such an arrangement would be impossible because of the size of the inspection optics. The means by which this is accomplished in the present system are described in more detail hereafter.

Figure 1:
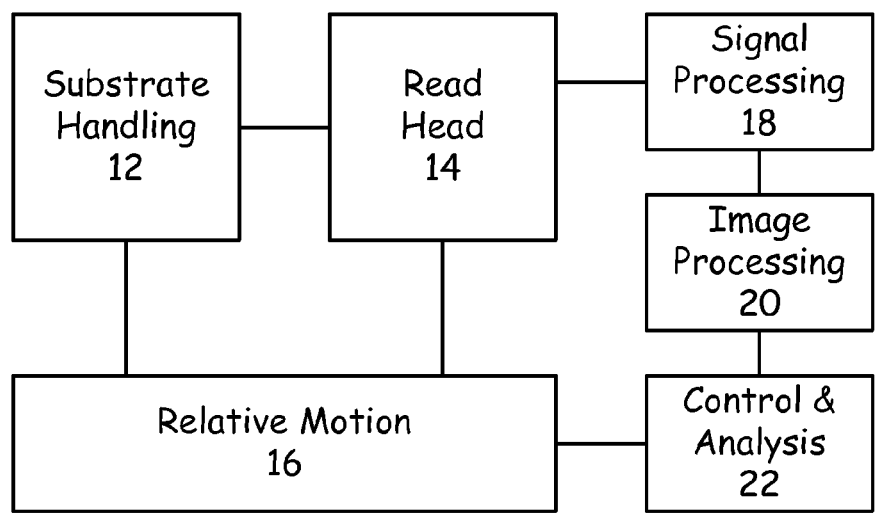
FIG. 1 is a functional block diagram of an inspection system according to an embodiment of the present invention.

With reference now to FIG. 1, there is depicted a functional block diagram of an inspection system 10 according to an embodiment of the present invention. The inspection system 10 illustrated includes a substrate handling subsystem 12. The substrate handling system 12 preferably does not remove the substrate from the cassette 40 (depicted in FIG. 7) in which it is initially disposed. Rather, the substrate handling system 12 has one component that engages and retains the cassette 40, and in some embodiments a second component that engages and retains the substrate within the cassette 40.

Figure 7:
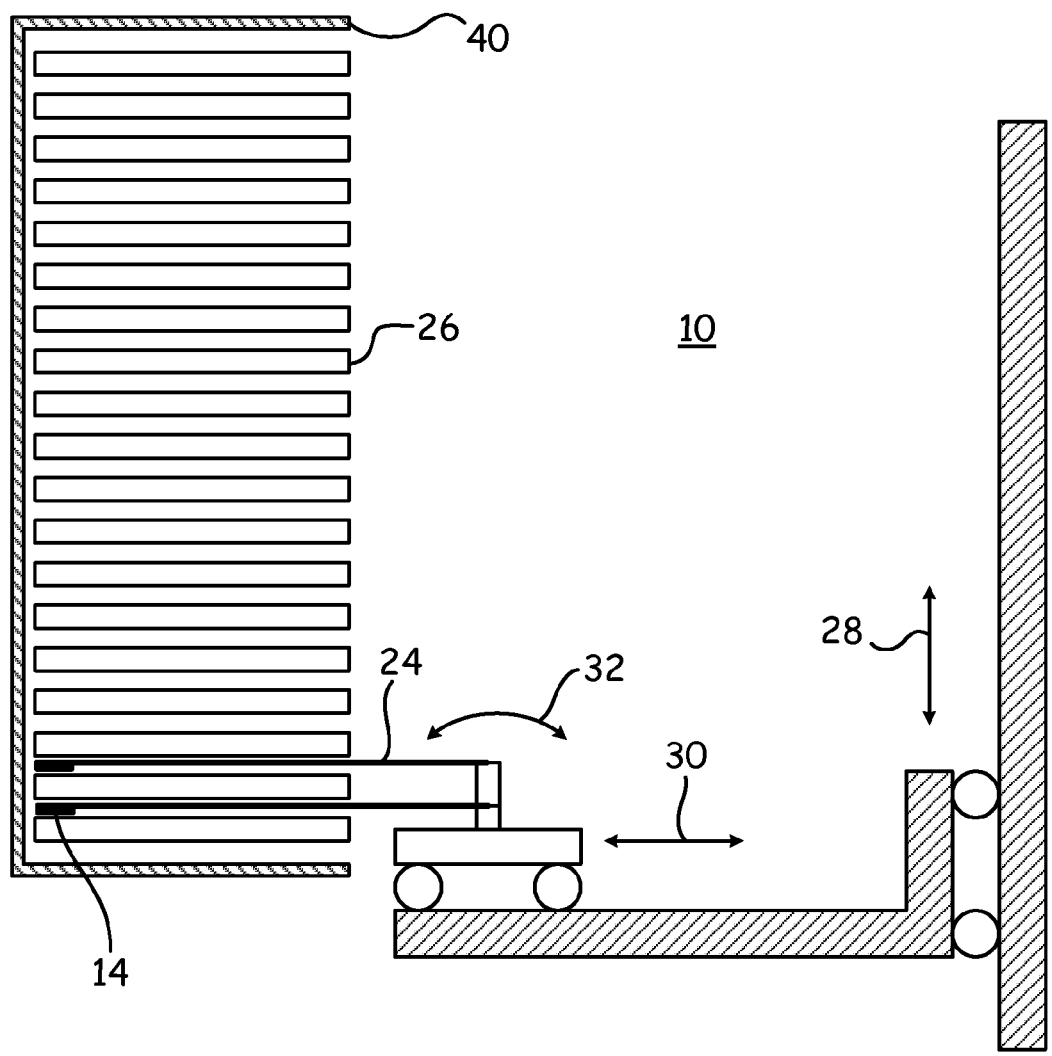
FIG. 7 is a representation of an inspection system according to an embodiment of the present invention.

For example, the first component that engages and retains the cassette 40 is, in one embodiment, a cassette 40 elevator. Substrates are typically disposed within slots that are formed in the cassette 40, in an orientation where the front of a first substrate is facing the back of the next substrate, and so on, as generally depicted in FIG. 7. Cassettes 40 may hold any number of substrates, such as twenty-five. An elevator is a device that engages and retains a cassette 40, typically with the substrates held in a horizontal orientation, and can then move up and down in steps, so as to index the position of the cassette 40 and dispose each substrate in turn at a given elevation. This is referred to as movement in the Z direction. In some embodiments the first component is operable to translate the cassette 40 in an X direction. Also, in some embodiments the first component is operable to translate the cassette 40 in a Y direction.

The second component that is present in some embodiments has one or more different functions. In one embodiment the second component holds the substrate within the cassette 40 and prevents it from moving. In another embodiment the second component rotates the substrate, either in only one direction, or selectively in either direction. In some embodiments the second component is not provided at all, such as when gravity alone is used to keep the substrate in place within the cassette 40.

The first and second components of the relative motion means 16 are used in one embodiment to align the substrates to a given orientation prior to being inspected. In other embodiments, this alignment is accomplished using other equipment prior to placing the cassette 40 in the inspection system 10. In yet other embodiments, no physical prealignment of the substrates 40 is performed at all. In some of these embodiments, a virtual alignment of the substrate 26 is performed, such as after an image of the substrate 26 is formed, as described in more detail hereafter.

Figure 2:
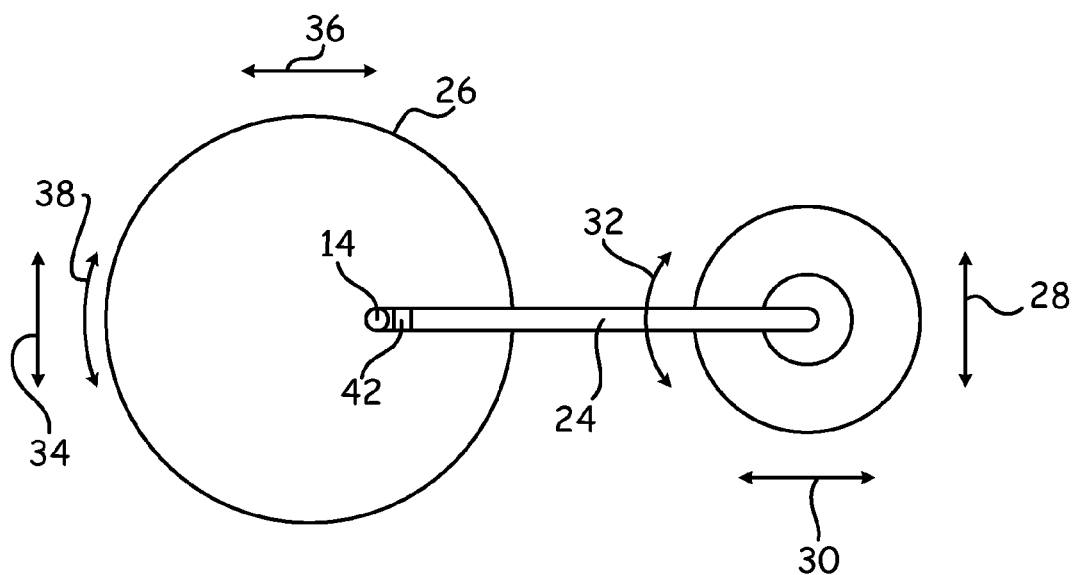
FIG. 2 is a representation of motion between a substrate under inspection and a read head of an inspection system according to an embodiment of the present invention.

A read head 14 is provided to inspect the substrate. The read head 14 is disposed on an armature 24 (as depicted in FIG. 2), which in one embodiment has a length that is sufficient to dispose the read head 14 at any desired point across the surface of the substrate 26. Further, both the read head 14 and the armature 24 in one embodiment are sized such that they fit between adjacent substrates 26 as they reside within the cassette 40. In this manner, the read head 14 can be used to inspect a substrate 26 without removing the substrate 26 from the cassette 40.

Means 16 are provided in some embodiments to provide relative motion between the substrate 26 and the read head 14. This may take the form of moving one or both of the read head 14 and the substrate 26, as depicted in FIG. 2. In various embodiments, the relative motion system 16 provides one or more of the motions indicated in FIG. 2, which include translation of the read head 14 in the Y direction 28, translation of the read head 14 in the X direction 30, rotation or sweeping back and forth of the read head 14 in a rotary manner 32, translation of the substrate 26 in the Y direction 38, translation of the substrate 26 in the X direction 36, and rotation of the substrate 26 in either one or both directions in a rotary manner 38.

By moving one or both of the substrate 26 and the read head 14 relative to other, while the substrate 26 remains within the cassette 40, a desired portion of the substrate 26 can be inspected, where the desired portion can include anything from a single point on the substrate 26 up to the entire surface of the substrate 26.

Figure 3:
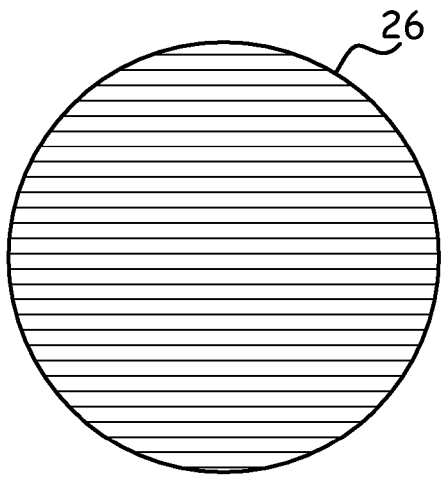
FIG. 3 is a representation of scan lines in an inspection pattern on a substrate according to a first embodiment of the present invention.

FIGS. 3-6 illustrate various scan patterns that are possible with the inspection system 10. For example, FIG. 3 depicts a horizontal linear scan pattern. This scan pattern could be formed by a variety of different embodiments of the system 10. For example, the scan pattern could be formed by moving the read head 14 in and out of the cassette 40, indexing the position of the read head 14 as each scan line is completed, and while holding the substrate 26 motionless or allowing it to just reside within the cassette 40 without any additional means to hold it motionless.

In another embodiment, the cassette 40 could be moved back and forth in a similar manner, while the read head 14 is held motionless. In yet another embodiment, the read head 14 is moved in an out, while the cassette 40 is translated in the X direction 24 to provide the index between the scan lines. Thus, it is appreciated that the scan pattern could be provided in a great variety of different ways.

Figure 4:
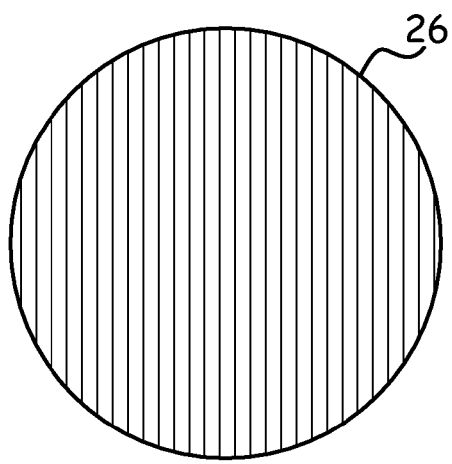
FIG. 4 is a representation of scan lines in an inspection pattern on a substrate according to a second embodiment of the present invention.

FIG. 4 depicts a vertical scan pattern, which could be formed in much the same manner as the pattern described in regard to FIG. 3. Once again, motion for the scan pattern could be provided entirely by the read head 14, entirely by the substrate 26 as it resides within the cassette 40, or by a combination of the two.

Figure 5:
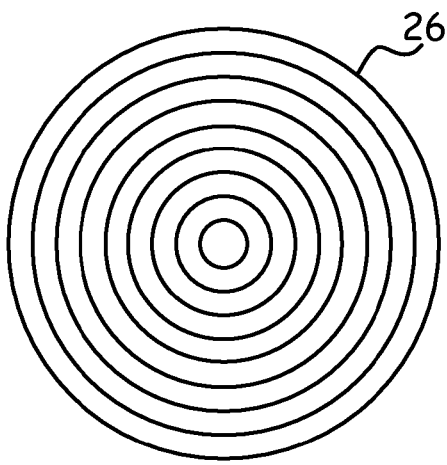
FIG. 5 is a representation of scan lines in an inspection pattern on a substrate according to a third embodiment of the present invention.

Yet another scan pattern is depicted in FIG. 5, where concentric circles of scan lines are used to form the scan pattern. This scan pattern could be formed, for example, by rotating the substrate 26 in a desired direction 38 while it resides within the cassette 40, and as one circumference is completed, either translating the cassette 40 in direction 36 or 38 so as to index the scan pattern, or translating the read head 14 in direction 28 or 30, or sweeping 32 the read head 14 across the surface of the substrate 26, so as to index the scan pattern. In some embodiments only one of these motions is used, and in other embodiments a combination of these motions are used to produce the scan pattern.

Figure 6:
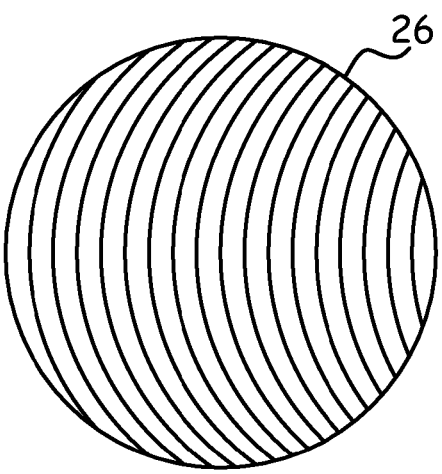
FIG. 6 is a representation of scan lines in an inspection pattern on a substrate according to a fourth embodiment of the present invention.

FIG. 6 depicts another scan pattern, which can be formed such as by sweeping 32 the read head 14 back and forth across the surface of the substrate 26 as is resides within the cassette 40, and then translating either the cassette 40 or the read head 14 to create the indexing between the scan lines of the scan pattern. As before, the desired motion can be created in a great variety of different ways.

In some embodiments only the read head is operable to move in the X and Y directions, such as by translations 28 and 30 and sweeps 32, while the cassette 40 only moves during inspection operations in the Z direction, such as to step from one substrate 26 to another. In other embodiments, this motion in the Z direction is accomplished by the read head 14, and the cassette 40 doesn't move at all during inspection operations, although it may move during operations whereby it is loaded and loaded from the inspection system. In some of these embodiments, the substrates 26 and cassette 40 are retained in the system 10 by gravity alone.

FIG. 7 depicts a simple embodiment of the inspection system 10, where the read head 14 is moved during the inspection operations. The embodiment of FIG. 7 also depicts an embodiment of the inspection system 10 that has multiple read heads 14, which can be used to inspect more than one substrate at a time. In some embodiments, the read head 14 has multiple channels, such as multiple sensors, which can simultaneously sense either multiple properties of the substrate 26 or can sense the same property separately.

The rate of movement is, in some embodiments, in a range of from several cycles (scan lines) per second to several tens of cycles per second, in order to scan the entire substrate 26 within from about one minute to about five minutes, which is dependent at least in part upon the size of the substrates 26 to be scanned. The movement in some embodiments is also carefully controlled so as to not run off the edge of the substrate 26 or hit the sides of the cassette 40.

The read head 14 and armature 24, in one embodiment, have properties similar to a hard disk drive head slider. The read head 14 in this and some other embodiments contains the imaging optics. It sweeps back and forth across the substrate 26 to build up an image of the surface of the substrate 26.

In one embodiment the read head 14 moves across the surface of the substrate 26 on an air bearing 42 (depicted in FIG. 2) that maintains a constant distance between the read head 14 and the surface of the substrate 26, and thereby maintains focus control. The fly height of the read head 14 can, in this embodiment, be adjusted by adjusting the air bearing 42 pressure, thus providing a control on the focus. The lens of the read head 14 can be similar to that used in a CD or DVD player.

In one embodiment, light is coupled in to and out from the read head 14 through fiber optic cables. The optics can be set up in a bright field mode, such as for macro-inspection, or in a dark field mode, such as for particle inspection. For higher throughput, a multi-channel design can be employed, such as by using multiple fiber channels, with either one larger lens or multiple mini-lenses on the read head 14. Other applications, such as layer thickness monitoring, could be enabled, such as through spectroscopic analysis.

A signal processing unit 18 receives the electrical or optical signals from the read head 14, and provides image data to an image processing unit 20. The image processing unit 20 assembles the incoming data stream into an X-Y image and, in some embodiments, provides a coordinate transform to convert the image from its original form, such as circular, polar, or curvilinear coordinates, to X-Y Cartesian coordinates. This information is provided to a control and analysis unit 22, which controls the various functions of the inspection system 10, and performs various comparisons (such as die to die, substrate to substrate, or absolute gray level) to detect defects of interest or process issues. Depending on the resolution and data rate of the inspection system 10, the image processing system 20 and the control and analysis system 22 may be a single processing node, such as a personal computer, or for higher resolutions and throughput, a cluster of processing nodes.

By leaving the substrate 26 within the cassette 40, the various embodiments of the present invention save the time that is otherwise required for transporting and aligning the substrate 26 within the inspection system 10, along with the associated cost of the robotics. Using miniaturized lenses in the read head 14 and controlling the working distance with an air bearing 42 reduces the cost and complexity of the optics and associated supporting mechanics, such as a Z-focus stage.

As introduced above, various embodiments of the inspection system 10 are amenable to a variety of applications, such as (but not limited to) particle inspection, pattern inspection, overlay metrology, critical dimension metrology or scatterometry, film thickness measurement, and surface flatness measurements.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A substrate inspection system comprising:
   a cassette elevator for receiving a cassette of substrates, where multiple substrates are removably disposed within the cassette in a planar-spaced orientation, the cassette elevator for indexing a position of the cassette and selectively disposing a substrate at a given elevation, and
   an optical read head for insertion between adjacent substrates at the given elevation, such that the substrate is inspected at the given elevation while the substrates are disposed within the cassette, where the optical read head is of a size to fit between the adjacent substrates within the cassette.

2. The substrate inspection system of claim 1, wherein relative movement between the substrate and the read head produces scan lines that are assembled into an inspection image of the substrate.

3. The substrate inspection system of claim 1, wherein movement of only the substrate relative to the read head produces scan lines that are assembled into an inspection image of the substrate.

4. The substrate inspection system of claim 1, wherein movement of only the read head relative to the substrate produces scan lines that are assembled into an inspection image of the substrate.

5. The substrate inspection system of claim 1, wherein movement of both the substrate and the read head produces scan lines that are assembled into an inspection image of the substrate.

6. The substrate inspection system of claim 1, further comprising an air bearing disposed on the read head, where the air bearing rides along the surface of the substrate and sets a working distance between the substrate and the read head.

7. The substrate inspection system of claim 1, further comprising multiple read heads, where the substrate inspection system is operable to simultaneously inspect more than one substrate while the substrates are disposed within the cassette.

8. The substrate inspection system of claim 1, further comprising multiple sensors within the read head, where the multiple sensors simultaneously sense multiple channels of information from the substrate.

\* \* \* \* \*